United States Patent
Yamazaki et al.

(10) Patent No.: US 6,768,112 B2
(45) Date of Patent: Jul. 27, 2004

(54) SUBSTRATE INSPECTION SYSTEM AND METHOD FOR CONTROLLING SAME

(75) Inventors: Yuichiro Yamazaki, Tokyo-To (JP); Motosuke Miyoshi, Tokyo-To (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/026,727

(22) Filed: Dec. 27, 2001

(65) Prior Publication Data

US 2002/0084411 A1 Jul. 4, 2002

(30) Foreign Application Priority Data

Dec. 28, 2000 (JP) ........................................ 2000-400814

(51) Int. Cl.[7] ........................... G01N 23/00; G21K 7/00; A61N 5/00; G21G 5/00
(52) U.S. Cl. ................. 250/310; 250/492.1; 250/492.2; 250/492.3
(58) Field of Search ............................ 250/310, 492.1, 250/492.2, 492.3

(56) References Cited

U.S. PATENT DOCUMENTS

| | | | | |
|---|---|---|---|---|
| 5,578,821 A | * | 11/1996 | Meisberger et al. | 250/310 |
| 6,038,018 A | * | 3/2000 | Yamazaki et al. | 356/237.1 |
| 6,043,490 A | * | 3/2000 | Sakai | 250/310 |
| 6,172,363 B1 | * | 1/2001 | Shinada et al. | 250/310 |
| 6,310,341 B1 | * | 10/2001 | Todokoro et al. | 250/305 |
| 6,329,826 B1 | * | 12/2001 | Shinada et al. | 324/751 |
| 6,518,582 B1 | * | 2/2003 | Kohama | 250/492.2 |

FOREIGN PATENT DOCUMENTS

| | | |
|---|---|---|
| JP | 5-258703 | 10/1993 |
| JP | 6-188294 | 7/1994 |
| JP | 7-249393 | 9/1995 |
| JP | 11-132975 | 5/1999 |
| JP | 2000-286310 | 10/2000 |

* cited by examiner

*Primary Examiner*—Nikita Wells
*Assistant Examiner*—Mary El-Shammaa
(74) *Attorney, Agent, or Firm*—Finnegan, Henderson, Farabow, Garrett & Dunner L.L.P.

(57) ABSTRACT

A substrate inspection system includes: a charged particle beam irradiation part; an electron image detecting part; a mapping projecting part which projects the secondary and/or reflected charge particle generated from a substrate on the electron image detecting part; and a control part. The electron image detecting part includes a charged particle multiplying device which has an entrance surface for the secondary and/or reflected charged particle, and an image grabbing element having a fluorescent body with a light receiving surface to receive the multiplied secondary and/or reflected charged particle and a fluorescent surface on which an optical image appears. The control part causes the fluorescent surface of the fluorescent body to be grounded and applies a first negative potential to the entrance surface of the charged particle multiplying device.

20 Claims, 5 Drawing Sheets

SUBSTRATE INSPECTION SYSTEM AND METHOD FOR CONTROLLING SAME

CROSS REFERENCE TO RELATED APPLICATION

This application claims the benefit of priority from the prior Japanese Patent Application No. 2000-400814, filed on Dec. 28, 2000, the entire contents of which are incorporated herein by reference.

BACKGROUND OF THE INVENTION

1. Field of the Invention

The present invention generally relates to an inspection system and a method for controlling the same. More specifically, the invention relates to a substrate inspection system for observing an integrated circuit pattern on a semiconductor wafer by using charged particle beams.

2. Description of the Related Art

With the high integration of LSIs, the detection sensitivity required to detect defects and foreign matters on wafers and masks are rising. It is said that the detection sensitivity must be generally ½ or less of a pattern wiring width in order to inspect pattern defects and foreign matters which cause critical failures. For that reason, in a defect inspection on a semiconductor wafer which has a design rule of 0.13 $\mu$m or less, the limitation of the pattern defect inspection based on optical systems is realized. Under such a background, pattern defect inspection systems using charged particle beams have been developed (Japanese Patent Laid-Open Nos. 5-258703, 6-188294, 7-249393, etc.). In order to achieve a high-speed processing in a semiconductor wafer pattern inspection system based on charged particle beams, it is expected that the construction of an electron optical system proposed by Japanese Patent Laid-Open No. 7-249393 is the most influential means. In order to realize it, there is an optical system proposed by Japanese Patent Laid-Open No. 11-132975.

Figure 3:
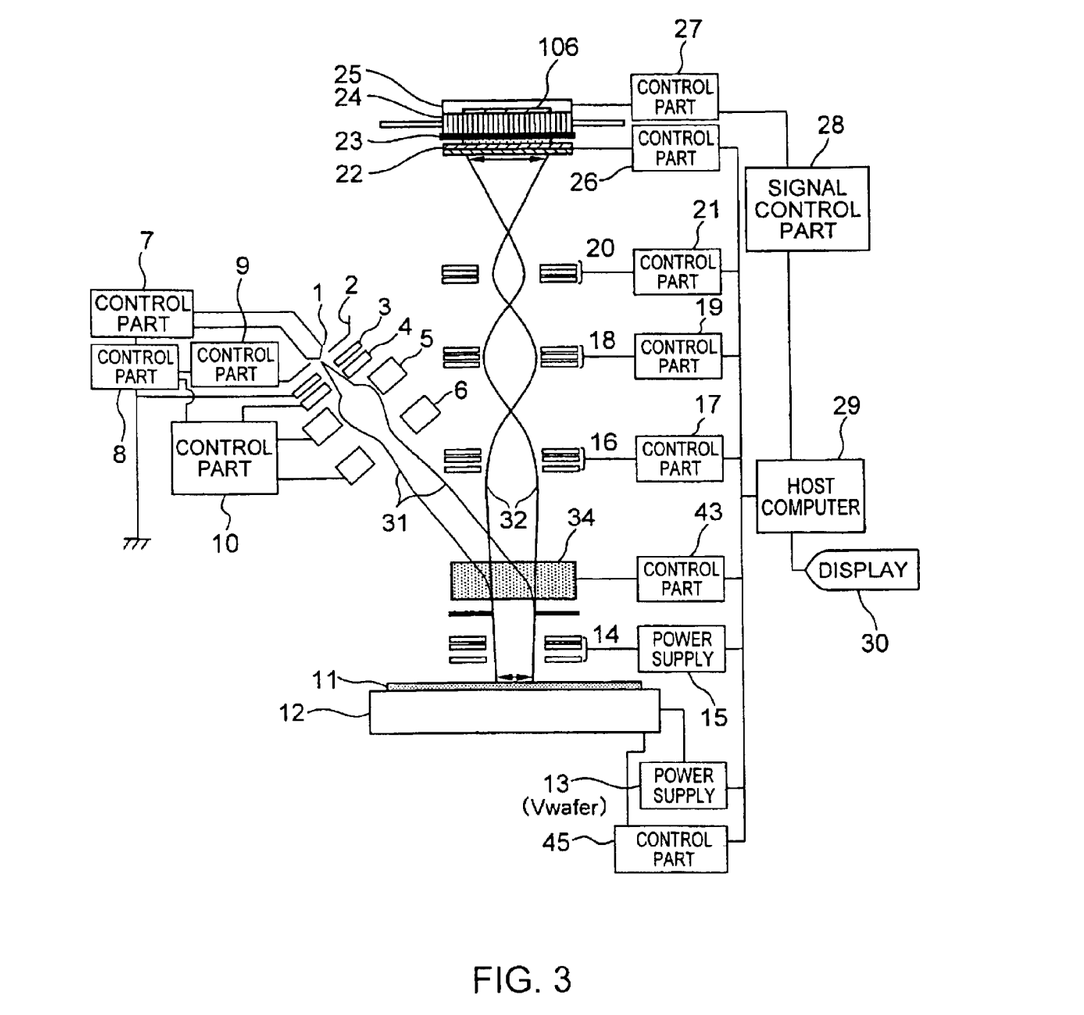
FIG. 3 is a block diagram showing a schematic construction of an example of a conventional substrate inspection system.

Referring to FIG. 3, a technique described in Japanese Patent Laid-Open No. 11-132975 will be described as an example of a related art. Furthermore, the same reference numbers are given to the same portions in the respective figures, and the detailed descriptions thereof are omitted.

A substrate inspection system shown in FIG. 3 uses electron beams as charged particle beams, and schematically comprises: an electron beam irradiation part, and a control part thereof; a stage 12 for mounting thereon a substrate 11 serving as a sample, and a control part thereof; a secondary, reflected and back-scattered electron beam mapping projecting optical part (which will be hereinafter simply referred to as a mapping projecting optical part), and a control part thereof; an electron image detecting part, and a control part thereof; and an electron beam deflecting part, and a control part thereof.

The electron beam irradiation part is arranged so as to be mechanically inclined with respect to the surface of the substrate 11. On the other hand, the optical axis of the mapping projecting optical part is arranged so as to extend in a direction perpendicular to the surface of the substrate 11. With this construction, electron beams (which will be hereinafter referred to as irradiation electron beams) 31 emitted from an electron gun enter the electron beam deflecting part in a direction inclined by a predetermined angle with respect to the surface of the sample, and the irradiation electron beams 31 are deflected by the electron beam deflecting part in a direction perpendicular to the surface of the substrate 11 to enter the substrate 11. In addition, secondary electrons, reflected electrons and back-scattered electrons (which will be hereinafter referred to as secondary electrons and so forth), which are produced on the surface of the substrate 11, are accelerated by the electric field on the surface of the substrate 11 in a direction perpendicular to the surface of the substrate 11 and enter the mapping projection optics.

The electron beam irradiation part comprises an electron gun and two-stage quadrupole lenses. The electron gun includes a lanthanum hexaboride (which will be hereinafter referred to as $LaB_6$) cathode 1 having a rectangular electron emission surface with the size of 100 $\mu$m×10 $\mu$m, an Wehnelt electrode 2 having a rectangular opening, an anode 3 having a rectangular opening, and a deflecting system 4 for adjusting an optical axis. The accelerating voltage, emission current and optical axis for the irradiation electron beams 31 are controlled by control parts 7, 8 and 9, respectively. In order to form rectangular beams having a size of 100 $\mu$m×25 $\mu$m on the surface of the substrate 11, two-stage electrostatic quadrupole lenses 5 and 6, and a control part 10 thereof are provided. The accelerating voltage for the irradiation electron beam 31 is determined by the relationship between the resolution of the mapping projecting optical part and the incidence voltage to the substrate 11.

The irradiation electron beams 31 are emitted from the $LaB_6$ cathode 1 to leave the electron beam irradiation part while being converged by the quadrupole lenses 5 and 6, and enter the electron beam deflecting part 34. The electron beam deflecting part 34 has a Wien filter (not shown). The trajectory of irradiation electron beams 31 is deflected by the Wien filter so as to be perpendicular to the surface of the substrate 11, and then, the irradiation electron beams 31 leave the electron beam deflecting part 34. Thereafter, the irradiation electron beams 31 are reduced by a rotationally symmetric electrostatic lens 14 to perpendicularly irradiate the substrate 11. A voltage is applied to the electrostatic lens 14 by a power supply 15.

A negative voltage is applied to the stage 12 by a power supply 13, so that a negative voltage is applied to the substrate 11. The movement of the stage 12 is controlled by a control part 13. The value of the voltage applied to the substrate 11 is determined by the resolution performance of the mapping projecting optical part. In order to obtain a resolution of 0.1 $\mu$m or less, the voltage of electron beams of secondary ions (which will be hereinafter referred to as secondary electron beams) 32 require energy of about 5 keV, so that a voltage applied to the sample is preferably 5 kV. On the other hand, the energy of the irradiation electron beams 31 is determined by the difference between the voltage applied to the substrate and the incident voltage to the substrate. If the substrate 11 is a semiconductor wafer, the incident voltage to the substrate 11 is generally about 800 V or less to prevent the irradiation damage and charging. As a result, the voltage of the irradiation electron beams is 5.8 kV.

When the wafer is irradiated with the irradiation electron beams 31, secondary electrons and so forth forming an electron image indicative of the shape, material, potential and so forth of the surface of the substrate are emitted from the surface of the substrate 11. These electrons are accelerated by an accelerating field produced between the electrostatic lenses 14 and enter the electron beam deflecting part 34 while drawing a trajectory having a focal point at infinity by the electrostatic lens 14. The electron beam deflecting part 34 is controlled on the conditions that the secondary electron beams 32 incident from the substrate 11 are caused to travel straight, and the secondary electron beams travel straight in the deflecting part 34 to enter a spectral means. Of energy of the secondary electron beams 32 produced from the substrate 11, only secondary electron beams having energy of a predetermined value or more enter the mapping projecting optical part.

The mapping projecting optical part includes three-stage rotationally symmetric electrostatic lenses 16, 18 and 20. The secondary electron beams 32 are enlarged to be projected by the electrostatic lenses 16, 18 and 20 to form an image on the electron image detecting part. The control parts 17, 19 and 21 control the voltages of the electrostatic lenses 16, 18 and 20, respectively.

The electron image detecting part includes an MCP (Micro Channel Plate) detecting device 22, a fluorescent screen 23, an FOP (Fiber Optical Plate) 24, a CCD element 106 and a CCD camera 25. In this embodiment, the CCD element 106 is a CCD area sensor. The secondary electron beams 32 entering the MCP detecting device 22 are multiplied 10,000 to 100,000 times by the MCP to irradiate the fluorescent screen 23, so that a fluorescent image is produced on the fluorescent surface. Thus, the electron image on the surface of the substrate 11 by means of the electron beams is converted into an optical image. This fluorescent image is detected by the CCD area sensor via the FOP 24 to be outputted as a picture signal from the CCD camera 25. The picture signal is fed to a host computer 29 via a signal control part 28, so that the image processing and the storage of image data are carried out. In addition, image data are displayed on a display 30 in the form of a two-dimensional image.

Figure 4:
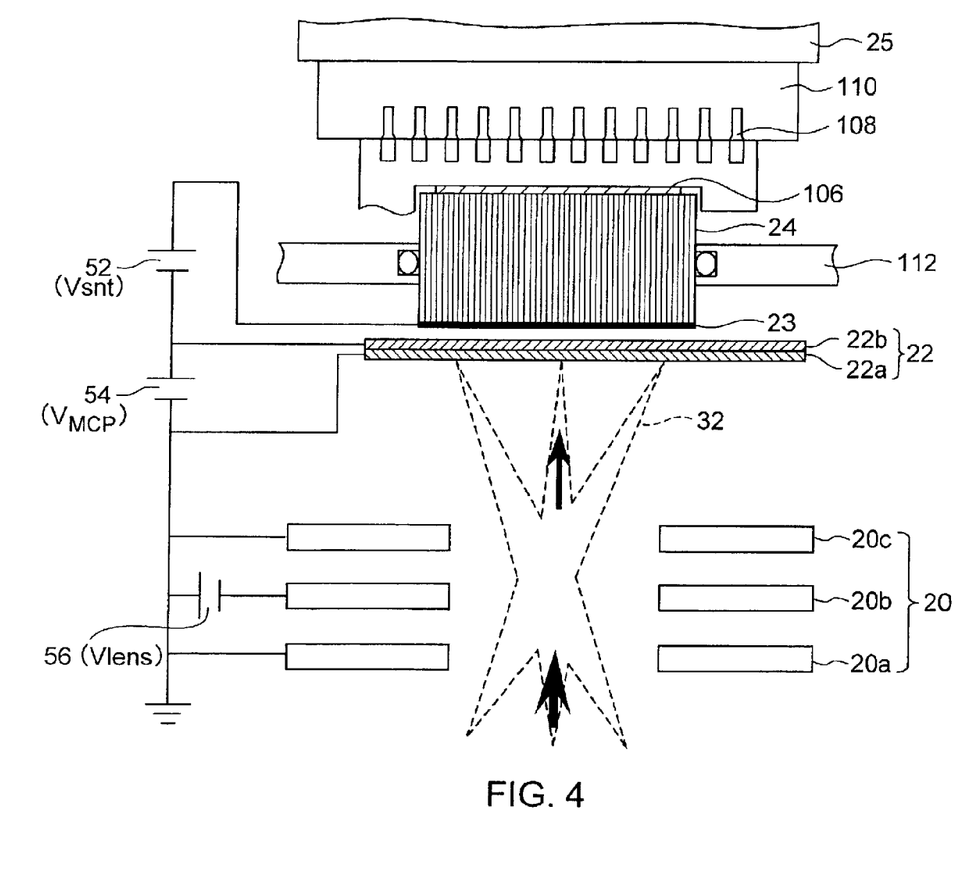
FIG. 4 is an illustration for explaining problems in the substrate inspection system shown in FIG. 3.
Figure 5:
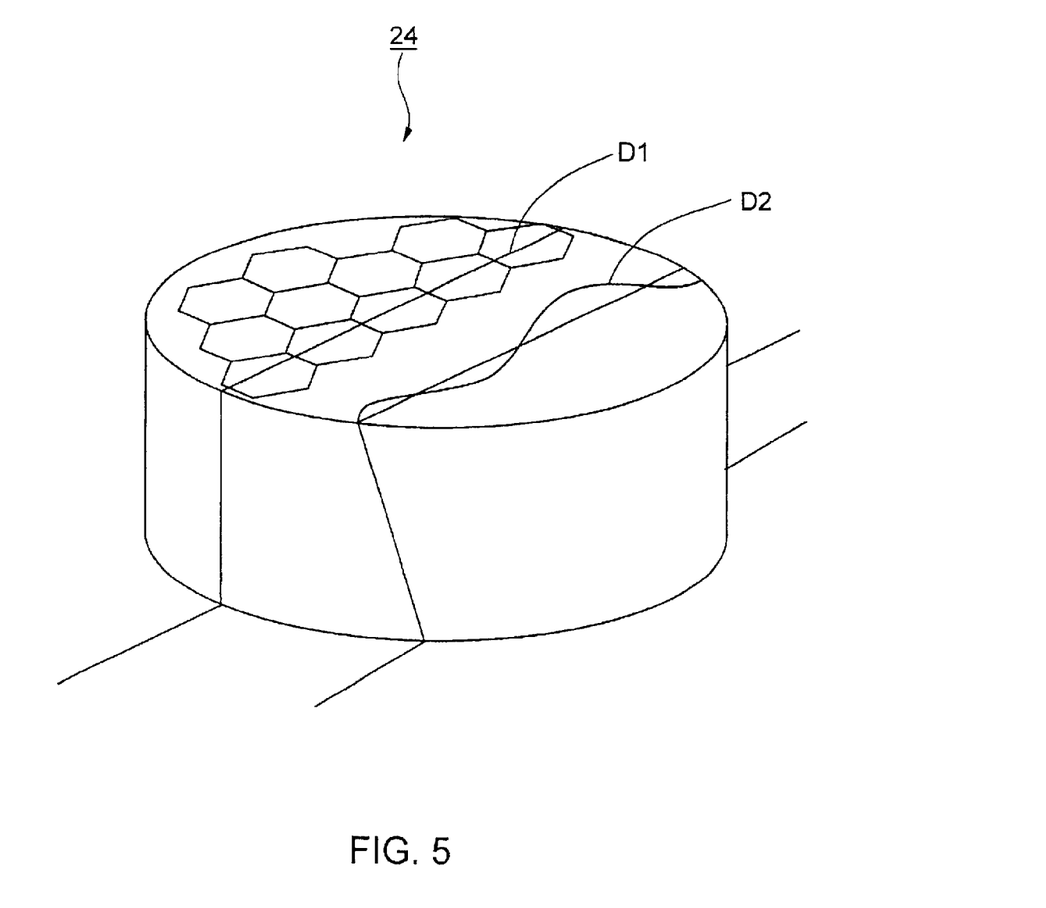
FIG. 5 is an illustration for explaining problems in an FOP of the substrate inspection system shown in FIG. 3.

However, in the conventional substrate inspection system, there is a problem in that the image deteriorates in a process for incorporating the electron image. Referring to FIGS. 4 and 5, this point will be described below. FIG. 4 is an illustration for explaining a technique for incorporating an image in the above described substrate inspection system described in Japanese Patent Laid-Open No. 11-132975. The electron image formed by the secondary electron beams 32 forms an image on the incident surface of the MCP 22 by electrostatic lenses 20a, 20b and 20c which are positioned at the final stage of the mapping projecting optical part. In more detail, the electron image detecting part includes MCPs 22a, 22b, the fluorescent screen 23, the FOP 24, the CCD element 106 and the CCD camera 25. In order to install the MCP 22 and the fluorescent screen 23 in a vacuum electron beam column, the separation of vacuum from the atmosphere is herein realized by clamping the FOP 24 by vacuum vessel walls 112. In order to obtain a higher gain, the MCP 22 comprises the combination of the two-stage MCPs 22a and 22b. The MCP 22 comprises a bundle of glass tubes which adhere to each other and each of which has an inside diameter of 10 μm or less and an air-core extending in longitudinal directions. On the inner surface of the tube, a material having high secondary electron emission efficiency is applied. The electron incident surface (the side of 22a) of the MCP 22 is grounded. On the other hand, the outgoing surface (the side of the MCP 22b) thereof is held at a positive potential by a power supply 54. Thus, an accelerating field extending from the incident surface to the outgoing surface exists in the tube. Electrons incident on the MCP 22 are multiplied while repeating scattering in each of the tubes of the first-stage MCP 22a, leave the outgoing surface of the MCP 22a and enter the second-stage MCP 22b to be further multiplied. Electrons emitted from the outgoing surface of the second-stage MCP 22b are accelerated toward the fluorescent surface of the fluorescent screen 23 by an accelerating field which is formed by a power supply 52, to irradiate the fluorescent surface to cause the fluorescent surface to emit light. Thus, the electron image formed on the incident surface of the MCP 22 can be converted into an optical image by causing light to be emitted from the fluorescent surface of the fluorescent screen 23 while multiplying the electron image by the MCP 22. The MCP 22 is a very effective means for improving S/N of the electron image since the MCP 22 can multiply electrons while maintaining the spatial resolution. The optical image produced on the fluorescent surface of the fluorescent screen 23 is detected by the CCD element 106 via the FOP 24 to be outputted as a picture signal from the CCD camera 25.

If a relay lens of an optical lens is adopted between the CCD element 106 and the fluorescent surface in order to incorporate the optical image, which is produced on the fluorescent surface, into the CCD element 106 in such an electron image detecting system, the optical system tends to be made large in order to prevent distortion. This is an obstacle to the request for the miniaturization of the system. In addition, the decrease of the transmittance due to the optical lens itself can not be ignored. The above described substrate inspection system is characterized in that the FOP 24 is adopted in this region to shorten the distance between the fluorescent surface of the fluorescent screen 23 and the CCD element 106 and to improve the transmittance. However, it is not easy to suppress distortion due to the method for producing the FOP. As shown in FIG. 5, distortions, such as a share distortion D1 and a gross distortion D2, exist in the FOP 24. It is very difficult to reduce these distortions. It is known that such distortions depend on the distance between the incident surface and outgoing surface of the FOP 24 and decrease in proportion to the decrease of the distance. However, the FOP 24 also has the function of causing the CCD element 106 to be electrically insulated from the light receiving surface by applying a high voltage of about +4 kV to the fluorescent surface. From this point, it is difficult to produce the FOP 24 so that the FOP 24 has a thickness of 5 mm or less. In the current FOP producing method, it is difficult to suppress the distortion of a FOP having a thickness of 5 mm to be 10 μm or less. This mainly causes image distortion. This means that if the pixel size of the CCD element is 16 μm, the distortion of the FOP is 0.625 pixels, and the resolution of the image of a region, in which the FOP is distorted, greatly deteriorates. Due to this partial deterioration of resolution, a false defect may occur in a defect inspection. In addition, with respect to both of the optical lens and the FOP, any optical component for transferring the optical image is provided between the fluorescent surface and the CCD element 106, so that it is not possible to avoid the deterioration of the spatial resolution. In the optical system shown in FIG. 4, the image is transferred from the MCP 22, FOP 24 and CCD camera 25, so that it is not possible to avoid the deterioration of the spatial resolution of the image. If an image having a line and space pattern of 0.2 μm is acquired by pixels of 1 μm, the MTF (Modulation Transfer Function) values, which are indexes indicative of optical characteristics, of the MCP 22, the FOP 24 and the CCD camera 25 are 0.43, 0.8 and 0.5, respectively. The MTF from the MCP 22 to the CCD camera 25 is a product of the respective MTFs ($MTF_{detector}=MTF_{MCP} \times MTF_{FOP} \times MTF_{CCD}$), so that $MTF_{detector}=0.172$ which is greatly deteriorated. In order to suppress such distortion of the MTF, it is required to simplify the construction for incorporating an optical image after an electron image is formed on the MCP 22.

SUMMARY OF THE INVENTION

According to a first aspect of the invention, there is provided a substrate inspection system comprising: a substrate mounting part for mounting thereon a substrate to be inspected; a charged particle beam irradiation part for generating a charged particle beam to irradiate the substrate with the charged particle beam, the irradiation of the charged particle beam causing a secondary charged particle and/or a reflected charged particle to generate from the substrate; an electron image detecting part for detecting an electron image which is formed by the secondary charged particle and/or the reflected charged particle and is indicative of a physical property of the surface part of the substrate and for outputting a picture signal of the image; the electron image detecting part including a charged particle multiplying device for multiplying the secondary charged particle and/or the reflected charged particle, and an image grabbing element having a fluorescent body for receiving the multiplied secondary charged particle and/or reflected charged particle as the electron image and for converting the electron image into an optical image, the image grabbing element converting the optical image into the picture signal; the charged particle multiplying device having an entrance surface through which the secondary charged particle and/or the reflected charged particle enter; the fluorescent body having a light receiving surface for receiving the multiplied secondary charged particle and/or reflected charged particle and a fluorescent surface on which the optical image appears; a mapping projecting part for projecting the secondary charged particle and/or the reflected charge particle in some degree of magnification on the electron image detecting part; an inspection part for inspecting the substrate on the basis of the picture signal; and a control part for causing the fluorescent surface of the fluorescent body to be grounded and for applying a first negative potential to the entrance surface of the charged particle multiplying device.

According to a second aspect of the invention, there is provided a method for controlling a substrate inspection system comprising: a substrate mounting part for mounting thereon a substrate to be inspected; a charged particle beam irradiation part for generating a charged particle beam to irradiate the substrate with the charged particle beam; an electron image detecting part for detecting an electron image which are formed by a secondary charged particle and/or a reflected charged particle which are produced from the substrate by irradiation with the charged particle beam and which is indicative of a physical property of the surface part of the substrate and for outputting a picture signal of the image; a mapping projecting part for projecting the secondary charged particle and/or the reflected charge particle in some degree of magnification on the electron image detecting part; and an inspection part for inspecting the substrate on the basis of the picture signal, the electron image detecting part including a charged particle multiplying device for multiplying the secondary charged particle and/or the reflected charged particle, and an image grabbing element having a fluorescent body for receiving the multiplied secondary charged particle and/or reflected charged particle as the electron image and for converting the electron image into an optical image, the image grabbing element converting the optical image into the picture signal, the charged particle multiplying device having an entrance surface through which the secondary charged particle and/or the reflected charged particle enter, the fluorescent body having a light receiving surface for receiving the multiplied secondary charged particle and/or reflected charged particle and a fluorescent surface on which the optical image appears, the method comprising: causing the fluorescent surface of the fluorescent body to be grounded, and applying a first negative potential to the entrance surface of the charged particle multiplying device.

DESCRIPTION OF THE PREFERRED EMBODIMENTS

Referring now to the accompanying drawings, an embodiment of a substrate inspection system according to the present invention will be described below.

Figure 1:
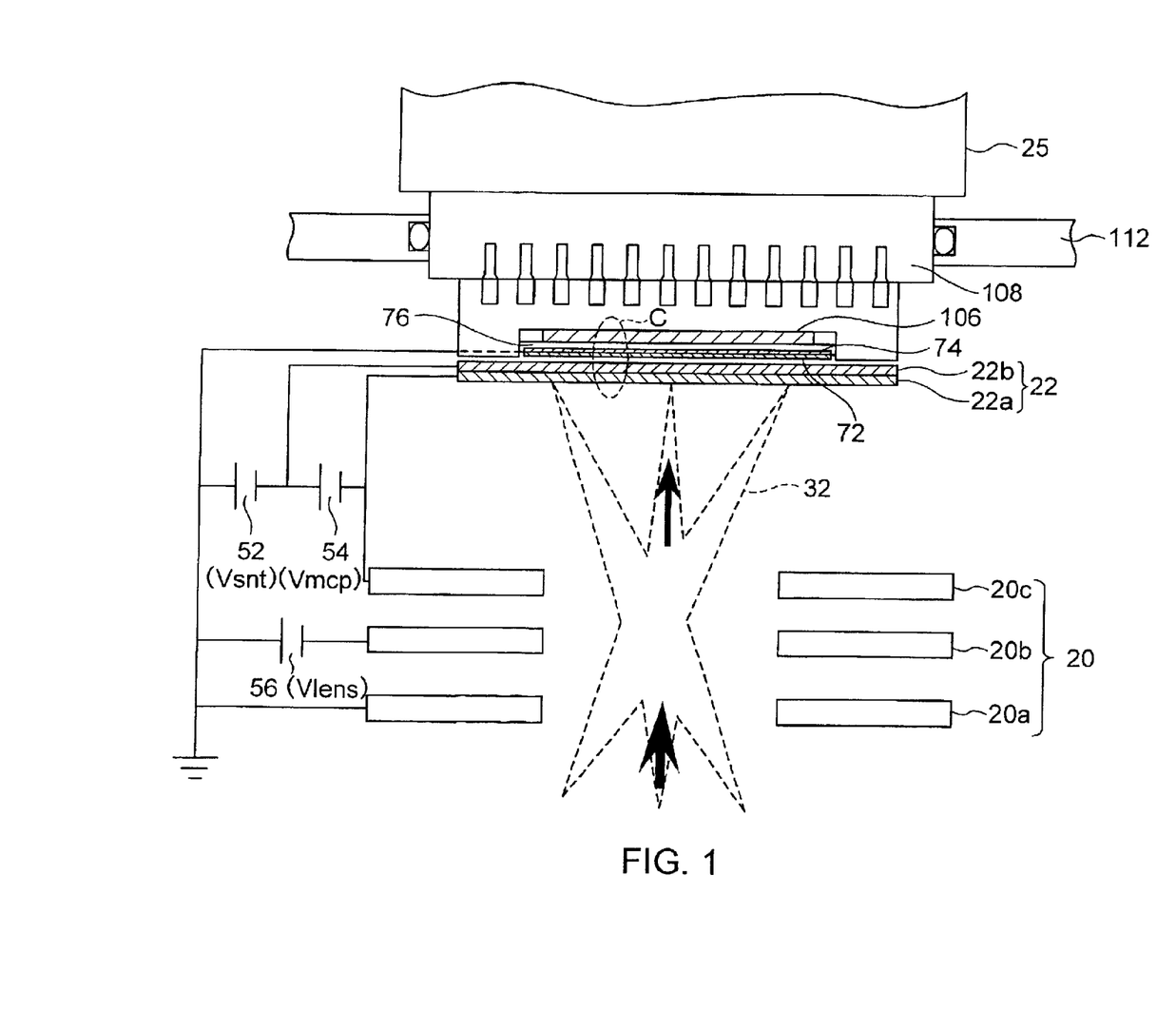
FIG. 1 is a block diagram showing a schematic construction of an electron image detecting part in an embodiment of a substrate inspection system according to the present invention.

FIG. 1 is a block diagram showing a schematic construction of an electron image detecting part in an embodiment of a substrate inspection system according to the present invention. The substrate inspection system in this embodiment is characterized by an electron image detecting part and a control part thereof. Other constructions of the substrate inspection system in this embodiment, i.e., an electron beam irradiation part and a control part thereof, a stage and a control part thereof, a mapping projecting optical part and a control part thereof, and an electron beam deflecting part and a control part thereof, are substantially the same as those of the substrate inspection system shown in FIG. 3, so that the electron image detecting part and the control part thereof serving as principal parts in this embodiment will be mainly described below.

The electron image detecting part shown in FIG. 1 does not include FOP. In the electron image detecting part, a light receiving surface for an optical image is integrally formed with a CCD element 106. A CCD camera 25 is clamped between vacuum vessel walls 112 in a socket portion 108. The CCD element 106 is installed in a vacuum vessel. As the CCD element 106, a line sensor, an area sensor, a TDI (Time Delay Integrator) sensor or the like may be selected. If the TDI sensor is used, an optical image can be incorporated in synchronism with the movement of a stage 12. Therefore, the use of the TDI sensor is very effective when a rapid inspection, such as a defect inspection for a semiconductor wafer, is required.

Figure 2:
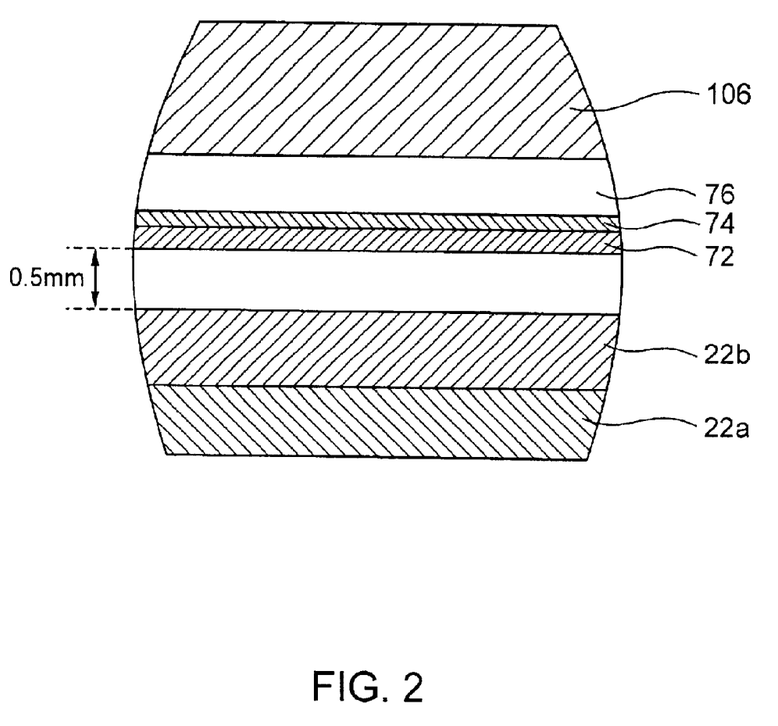
FIG. 2 is an enlarged view showing a principal part of the electron image detecting part shown in FIG. 1.

FIG. 2 is an enlarged view of a region C which is surrounded by broken lines in the electron image detecting part shown in FIG. 1. As shown in FIG. 2, the electron image detecting part in this embodiment includes a fluorescent body 72 which is provided on the side of an image grabbing surface of the CCD element 106 via a protective glass 76 and an Al thin film 74. The Al thin film 74 is formed by depositing Al on the protective glass 76 so as to have a thickness of about 10 $\mu$m. The fluorescent body 72 is formed by applying a fluorescent material on the Al deposited film 74 by the precipitation method. A two-stage MCP is arranged in the vicinity of the fluorescent body 72. The surface of the fluorescent body 72 serves as a surface for receiving electrons which are multiplied by the MCP 22. The distance between the electron outgoing surface of the second stage MCP 22b and the light receiving surface of the fluorescent body 72 is about 0.5 mm in this embodiment. Thus, the blurring of the electron image is inhibited.

Referring to FIG. 1 again, the Al thin film 74 is grounded. Thus, the Al thin film 72 has the function of preventing charging due to irradiation with electron beams and determining a potential on the fluorescent surface of the fluorescent body 72. In addition, a negative voltage Vsnt is applied to the outgoing surface of the MCP 22b by a power supply 52, to form an electric field so that the fluorescent surface of the fluorescent body 72 is arranged on the side of a positive potential with respect to the outgoing surface of the MCP 22b. Thus, electrons leaving the MCP 22b are accelerated. Moreover, a negative voltage (Vsnt+VMCP) is applied to the incident surface of the MCP 22a by power supplies 52 and 54 which are connected in series, to form an electric field so that the outgoing surface of the MCP 22b is arranged on the side of a positive potential with respect to the incident surface of the MCP 22a. Therefore, electrons incident on the MCP 22a are accelerated toward the outgoing surface of the MCP 22b and are multiplied while colliding with the inner wall of the tube of the MCP 22. In this embodiment, the above described voltage control for the MCP 22 and the fluorescent body 74 is carried out by a host computer 29 via a control part 26 (see FIG. 3).

As can be clearly from the comparison with FIG. 4, the incident surface of the MCP 22a is grounded in the conventional electron image detecting part, whereas the negative voltage (Vsnt+VMCP) with respect to the ground is applied to the incident surface of the MCP 22a in this embodiment. Since a voltage Vwafer is supplied to a substrate 11 by a power supply 13 (see FIG. 3), energy of secondary electron beams 32 incident on the MCP 22a is determined by the difference between the voltage (Vwafer) applied to the substrate 11 and the voltage (Vs+VMCP) applied to the incident surface of the MCP 22a. The incident energy Ein (eV) on the MCP 22a is as follows.

$$Ein(eV)=e(Vsnt+VMCP+Vwafer)$$

Due to the construction of the MCP 22, it has been revealed that the incident energy Ein (eV) is 2 keV or less.

Moreover, in this embodiment, the electrode of an electrostatic lens 20a of electrostatic lenses 20a through 20c constructing an Einzel lens is grounded, and a negative lens voltage Vlens is applied to the electrode of the electrostatic lens 20b by a power supply 56. In addition, the electrode of the electrostatic lens 20c is connected to the series connection of the power supplies 52 and 54, and the same voltage (VS+VCMP) as the voltage applied to the incident surface of the MCP 22a is applied. As the related art shown in FIG. 4, if the electrode of the electrostatic lens 20c is grounded, the secondary electron beams 32 are decelerated by a decelerating field, which is formed between the electrode of the electrostatic lens 20c and the incident surface of the MCP 22a, to be incident on the MCP 22a. In this case, the ununiformity of the decelerating field between the electrode of the electrostatic lens 20c and the MCP 22a deteriorates aberration performance to produce the blurring of the electron image. On the other hand, in this embodiment, the potential of the electrode of the electrostatic lens 20c is equal to the potential of the incident surface of the MCP 22a, the lens voltage Vlens is applied to the electrode of the electrostatic lens 20b, and the electrode of the electrostatic lens 20a is grounded. Therefore, the secondary electron beams 32 from the electrode of the electrostatic lens 20c to the incident surface of the MCP 22a move at a constant velocity, and the deceleration of the secondary electron beams 32 is carried out in the Einzel lens comprising the electrostatic lenses 20a through 20c. In this embodiment, such voltage control to the lens electrodes is carried out by the host computer 29 via the control part 21 (see FIG. 3). Thus, it is possible to suppress contribution to aberration.

According to the substrate inspection system in this embodiment, the FOP serving as an optical member for transferring the optical image obtained on the fluorescent surface to the CCD element 106 in the aforementioned related art can be omitted, so that it is possible to eliminate problems which are caused in the FOP, such as distortion of images, deterioration of MTF and deterioration of transmittance. Thus, it is possible to acquire electron images at a high resolution, so that it is possible to prevent a false defect from being produced in a substrate defect inspection, for example. As a result, the performance of the inspection system is greatly improved. Moreover, according to this embodiment, the CCD element 106 can be provided in vacuum, so that it is possible to further miniaturize and lighten the inspection system.

While the embodiment of the present invention has been described, the present invention should not be limited to the above described embodiment, but the invention can be modified in various ways without departing from the principle of the invention. For example, while the electron beam deflecting part has included the Wien filter in the above described embodiment, the substrate inspection system may have no Wien filter. In addition, while the substrate inspection system has used electron beams as charged particle beams in the above described embodiment, the present invention should not be limited thereto, but the invention may be applied to a substrate inspection system using, e.g., ion beams.

What is claimed is:

1. A substrate inspection system comprising:
   a substrate mounting part which mounts thereon a substrate to be inspected;
   a charged particle beam irradiation part which generates a charged particle beam to irradiate the substrate with the charged particle beam, the irradiation of the charged particle beam causing a secondary charged particle and/or a reflected charged particle to generate from the substrate;
   an electron image detecting part which detects an electron image which is formed by the secondary charged particle and/or the reflected charged particle and is indicative of a physical property of the surface part of the substrate and outputs a picture signal of the image; said electron image detecting part including a charged particle multiplying device which multiplies the secondary charged particle and/or the reflected charged particle, and an image grabbing element having a fluorescent body which receives the multiplied secondary charged particle and/or reflected charged particle as the electron image and which converts the electron image into an optical image, said image grabbing element converting the optical image into the picture signal; said charged particle multiplying device having an entrance surface through which the secondary charged particle and/or the reflected charged particle enter said charged particle multiplying device; said fluorescent body having a light receiving surface which receives the multiplied secondary charged particle and/or reflected charged particle and a fluorescent surface on which the optical image appears;
   a mapping projecting part which projects the secondary charged particle and/or the reflected charge particle in some degree of magnification on said electron image detecting part;

an inspection part which inspects the substrate on the basis of the picture signal; and a control part which causes said fluorescent surface of said fluorescent body to be grounded and which applies a first negative potential to the entrance surface of said charged particle multiplying device.

2. A substrate inspection system according to claim 1, wherein said control part applies a second negative potential to the substrate mounting part, the absolute value of said second negative potential being greater than the absolute value of said first negative potential.

3. A substrate inspection system according to claim 1, wherein said control part controls said mapping projecting part so that a potential at a position at which the secondary charged particle and/or the reflected charged particle leave said mapping projecting part is said first negative potential.

4. A substrate inspection system according to claim 2, wherein said control part controls said mapping projecting part so that a potential at a position at which the secondary charged particle and/or the reflected charged particle leave said mapping projecting part is said first negative potential.

5. A substrate inspection system according to claim 3, wherein said mapping projecting part includes three-stage electrostatic lenses which are provided in the vicinity of said electron image detecting part, of the three-stage electrostatic lenses a first-stage electrostatic lens being positioned nearest to the substrate mounting part, a third-stage electrostatic lens being positioned nearest to said charged particle multiplying device and a second-stage electrostatic lens being positioned between the first-stage electrostatic lens and the third-stage electrostatic lens, and said control part causes the first-stage electrostatic lens to be grounded, applies said first negative potential to the third-stage electrostatic lens and applies a third negative potential to the second-stage electrostatic lens, the absolute value of said third negative potential being smaller than the absolute value of said first negative potential.

6. A substrate inspection system according to claim 4, wherein said mapping projecting part includes three-stage electrostatic lenses which are provided in the vicinity of said electron image detecting part, of the three-stage electrostatic lenses a first-stage electrostatic lens being positioned nearest to the substrate mounting part, a third-stage electrostatic lens being positioned nearest to said charged particle multiplying device and a second-stage electrostatic lens being positioned between the first-stage electrostatic lens and the third-stage electrostatic lens, and said control part causes the first-stage electrostatic lens to be grounded, applies said first negative potential to the third-stage electrostatic lens and applies a third negative potential to the second-stage electrostatic lens, the absolute value of said third negative potential being smaller than the absolute value of said first negative potential.

7. A substrate inspection system according to claim 1, which further comprises a vacuum vessel for housing therein said substrate mounting part, said charged particle beam irradiation part, said mapping projecting part and said charged particle multiplying device in vacuum state, and wherein said image grabbing element is installed in said vacuum vessel.

8. A substrate inspection system according to claim 1, which further comprises a charged particle beam deflecting part which changes an incident angle of the charged particle beam on the substrate and which changes an angle with which the secondary charged particle and/or the reflected charged particle are incorporated into said mapping projecting part.

9. A substrate inspection system according to claim 1, wherein the value of said first negative potential is selected so that the energy at which the secondary charged particle and/or the reflected charged particle are incident on said charged particle multiplying device is approximately 2 keV or less.

10. A substrate inspection system according to claim 1, wherein said image grabbing element has a protective member formed of a glass material, and said fluorescent body is formed by coating a fluorescent material on the surface of said protective member.

11. A substrate inspection system according to claim 10, wherein said image grabbing element further has an electrode which is provided between said protective member and said fluorescent body, said fluorescent body being grounded via said electrode.

12. A substrate inspection system according to claim 1, wherein said image grabbing element includes a TDI (Time Delay Integrator) type CCD element.

13. A method for controlling a substrate inspection system comprising: a substrate mounting part which mounts thereon a substrate to be inspected; a charged particle beam irradiation part which generates a charged particle beam to irradiate the substrate with the charged particle beam; an electron image detecting part which detects an electron image which are formed by a secondary charged particle and/or a reflected charged particle which are produced from the substrate by irradiation with the charged particle beam and which is indicative of a physical property of the surface part of the substrate and which outputs a picture signal of the image; a mapping projecting part which projects the secondary charged particle and/or the reflected charge particle in some degree of magnification on said electron image detecting part; and an inspection part which inspects the substrate on the basis of the picture signal, said electron image detecting part including a charged particle multiplying device which multiplies the secondary charged particle and/or the reflected charged particle, and an image grabbing element having a fluorescent body which receives the multiplied secondary charged particle and/or reflected charged particle as the electron image and for converting the electron image into an optical image, said image grabbing element converting the optical image into the picture signal, said charged particle multiplying device having an entrance surface through which the secondary charged particle and/or the reflected charged particle enter said charged particle multiplying device, said fluorescent body having a light receiving surface which receives the multiplied secondary charged particle and/or reflected charged particle and a fluorescent surface on which the optical image appears, said method comprising:

causing the fluorescent surface of said fluorescent body to be grounded, and applying a first negative potential to the entrance surface of said charged particle multiplying device.

14. A method for controlling a substrate inspection system according to claim 13, which further comprises applying a second negative potential to the substrate mounting part, the absolute value of said second negative potential being greater than the absolute value of said first negative potential.

15. A method for controlling a substrate inspection system according to claim 13, which further comprises applying said first negative potential at a place at which the secondary charged particle and/or the reflected charged particle leave said mapping projecting part toward said electron image detecting part.

16. A method for controlling a substrate inspection system according to claim 14, which further comprises applying said first negative potential at a place at which the secondary charged particle and/or the reflected charged particle leave said mapping projecting part toward said electron image detecting part.

17. A method for controlling a substrate inspection system according to claim 15, wherein said mapping projecting part includes three-stage electrostatic lenses which are provided in the vicinity of said electron image detecting part, of the three-stage electrostatic lenses a first-stage electrostatic lens being positioned nearest to the substrate mounting part, a third-stage electrostatic lens being positioned nearest to said charged particle multiplying device and a second-stage electrostatic lens being positioned between the first-stage electrostatic lens and the third-stage electrostatic lens, and said method further comprises causing the first-stage electrostatic lens to be grounded, applying said first negative potential to the third-stage electrostatic lens and applying a third negative potential to the second-stage electrostatic lens, the absolute value of said third negative potential being smaller than the absolute value of said first negative potential.

18. A method for controlling a substrate inspection system according to claim 16, wherein said mapping projecting part includes three-stage electrostatic lenses which are provided in the vicinity of said electron image detecting part, of the three-stage electrostatic lenses a first-stage electrostatic lens being positioned nearest to the substrate mounting part, a third-stage electrostatic lens being positioned nearest to said charged particle multiplying device and a second-stage electrostatic lens being positioned between the first-stage electrostatic lens and the third-stage electrostatic lens, and said method further comprises causing the first-stage electrostatic lens to be grounded, applying said first negative potential to the third-stage electrostatic lens and applying a third negative potential to the second-stage electrostatic lens, the absolute value of said third negative potential being smaller than the absolute value of said first negative potential.

19. A method for controlling a substrate inspection system according to claim 13, which further comprises changing an incident angle of the charged particle beam on the substrate and changing an angle with which the secondary charged particle and/or the reflected charged particle are incorporated into said mapping projecting part.

20. A method for controlling substrate inspection system according to claim 13, wherein the value of said first negative potential is selected so that the energy at which the secondary charged particle and/or the reflected charged particle are incident on said charged particle multiplying device is approximately 2 keV or less.

* * * * *